(12) United States Patent
Tack et al.

(10) Patent No.: US 8,551,040 B2
(45) Date of Patent: Oct. 8, 2013

(54) MOTORIZED HEAD FOR A BREAST PUMP

(75) Inventors: Johannes W. Tack, Zuidhorn (NL); Michiel A. A. Schallig, Drachten (NL)

(73) Assignee: Koninklijke Philips N.V., Eindhoven (NL)

( * ) Notice: Subject to any disclaimer, the term of this patent is extended or adjusted under 35 U.S.C. 154(b) by 31 days.

(21) Appl. No.: 13/132,942

(22) PCT Filed: Dec. 11, 2009

(86) PCT No.: PCT/IB2009/055677
§ 371 (c)(1),
(2), (4) Date: Jun. 6, 2011

(87) PCT Pub. No.: WO2010/067331
PCT Pub. Date: Jun. 17, 2010

(65) Prior Publication Data
US 2011/0238007 A1    Sep. 29, 2011

(30) Foreign Application Priority Data
Dec. 12, 2008  (EP) .................................... 08171456

(51) Int. Cl.
*A61M 1/06*    (2006.01)
(52) U.S. Cl.
USPC ......................................................... 604/74

(58) Field of Classification Search
USPC ..................... 604/74–76; 417/321
See application file for complete search history.

(56) References Cited

U.S. PATENT DOCUMENTS

| 4,993,925 | A | 2/1991 | Becker et al. |
|---|---|---|---|
| 5,947,923 | A | 9/1999 | Uehara et al. |
| 6,974,440 | B2 | 12/2005 | Silver |
| 6,997,897 | B1 | 2/2006 | Silver et al. |
| 7,255,681 | B1 | 8/2007 | Silver et al. |
| 2005/0228342 | A1* | 10/2005 | Yuen .............................. 604/74 |
| 2010/0174232 | A1* | 7/2010 | Wortley et al. ................. 604/74 |

FOREIGN PATENT DOCUMENTS

EP    2155792 A    10/1985

\* cited by examiner

Primary Examiner — Quynh-Nhu H Vu (57) ABSTRACT

A motorised head (3) for a breast pump comprising a motor unit (35) including a motor and a drive mechanism (22) for driving a pump, a body mounting portion which is fixedly mountable to a body of a breast pump, a motor mounting portion (39) on which the motor and drive mechanism (22) are disposed, and a resiliently deformable member (49) connecting the body mounting portion and the motor mounting portion such that the resiliently deformable member reduces the transfer of vibration caused by the motor or drive mechanism to a breast pump body to which the body mounting portion is mounted.

15 Claims, 5 Drawing Sheets

MOTORIZED HEAD FOR A BREAST PUMP

FIELD OF THE INVENTION

The present invention relates to a motorised head for a breast pump and a hand held powered breast pump comprising a motorised head for a breast pump.

BACKGROUND OF THE INVENTION

Breast pumps are well known devices for extracting milk from a breast of a user. A breast pump may be used if the baby or infant is not itself able to extract the milk, or if the mother is separated from the baby or infant, for example, if away from the baby at work. Breast pumps may be manually operated, for example by squeezing a handle or operation of a foot pedal. Alternatively, breast pumps may be electrically driven by a small electric motor.

Conventional motorised breast pumps which are driven by a small electric motor operate by reciprocally driving a piston means for effecting pumping in the breast pump which creates a cyclic vacuum and/or mechanically stimulates the breast in order to promote the expression of milk therefrom. For milk expression to occur, a natural reflex called "letdown" must occur. This reflex is controlled by hormones, which allow the milk from the milk glands to be released into the milk ducts. Therefore, it is important that the user is relaxed and so the breast pump should operate in an as natural environment as possible to enable efficient and comfortable extraction of milk.

SUMMARY OF THE INVENTION

A disadvantage of conventional motorised breast pumps is that they produce a high level of noise and vibration when operated and so the ambiance created during operation of the breast pump is not natural and causes problems for many women with the "let-down" reflex. Furthermore, the high level of noise generated by conventional breast pumps prohibits many women from using a breast pump for expressing milk outside the privacy of their own home, because they are not able to use such an appliance in a discreet manner.

Therefore, there is a need for a motorised breast pump that minimises the noise level generated when said breast pump is operated.

The present invention seeks to provide a motorised head for a breast pump and a breast pump that reduces or substantially alleviates the problems and disadvantages associated with conventional breast pumps, as discussed above.

According to the present invention, there is provided a motorised head for a breast pump comprising a motor unit including a motor and a drive mechanism for driving a pump, a body mounting portion which is fixedly mountable to a body of a breast pump, a motor mounting portion on which the motor and drive mechanism are disposed, and a resiliently deformable member connecting the body mounting portion and the motor mounting portion such that the resiliently deformable member reduces the transfer of vibration caused by the motor or drive mechanism to a breast pump body to which the body mounting portion is mounted.

Preferably, the body mounting portion extends around a periphery of the body mounting portion.

Advantageously, a section of the resiliently deformable member extends parallel to an edge of the body mounting portion.

A section of the resiliently deformable member may extend parallel to an edge of the motor mounting portion.

In one embodiment, an arcuately extending aperture is defined between the motor mounting portion and the body mounting portion, and the resiliently deformable member extends there between.

The motorised head may further comprise a plurality of resiliently deformable members which connect the body mounting portion to the motor mounting portion.

Conveniently, two or three resiliently deformable members connect with the body mounting portion to the motor mounting portion.

In a preferred embodiment, the body mounting portion, the motor mounting portion and the resiliently deformable member are integrally formed.

The body mounting portion may be fixedly locatable against a locating surface on the body.

Advantageously, a face of the motor mounting portion is locatable against the locating surface on the body and the locating surface is resiliently deformable.

Advantageously, raised portions of said face are locatable against the locating surface of the body to minimise a contact area of said face against said locating surface.

In one embodiment, said face has a sinuous form and raised peaks of the face locate against the locating surface.

At least one flange may extend from the body mounting portion which may be configured to fixedly mount the motorised head to a body of a breast pump.

According to another aspect of the invention, there is provided a hand held powered breast pump comprising a body having a breast receiving portion and means for attaching a vessel to receive milk, piston means for effecting pumping and a pump head, wherein the drive mechanism may be configured to attach to the piston means.

Preferably, the piston means comprises a resilient diaphragm and the resiliently deformable locating surface is defined by an engaging part of said resilient diaphragm.

Preferably, said locating surface includes raised portions and the face of the motor mounting portion is configured to locate against said raised portions.

BRIEF DESCRIPTION OF THE DRAWINGS

Embodiments of the present invention will now be described by way of example only, with reference to the accompanying drawings, in which.

DETAILED DESCRIPTION OF THE DRAWINGS

Figure 1:
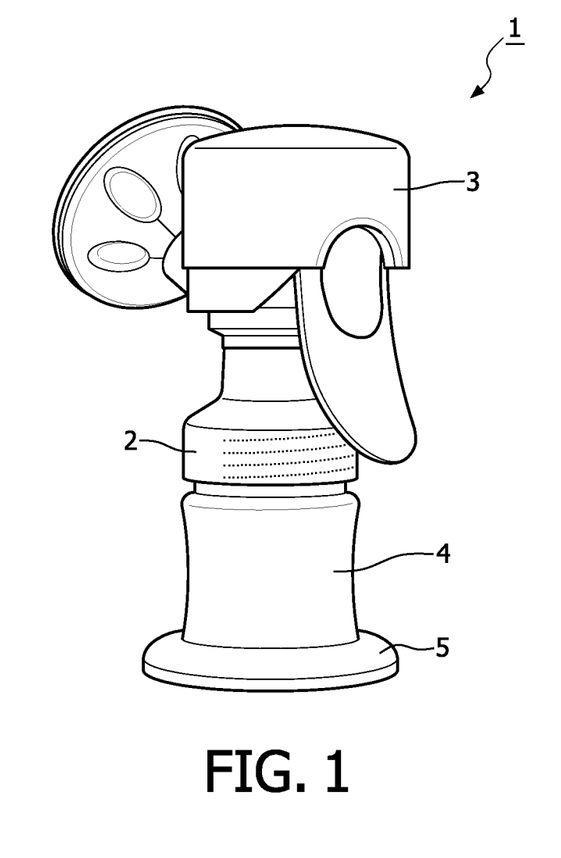
FIG. 1 is a side perspective view of a breast pump system according to one aspect of the present invention.

Referring now to the drawings, a breast pump according to one aspect of the present invention is shown in FIG. 1 comprising a body 2, a motorised head 3, a feeding bottle 4 and a base 5 for the feeding bottle 4.

The body 2 and the feeding bottle 4 are very similar to the components of the Avent® ISIS® breast pump product, although the invention is not limited thereto.

Figure 2:
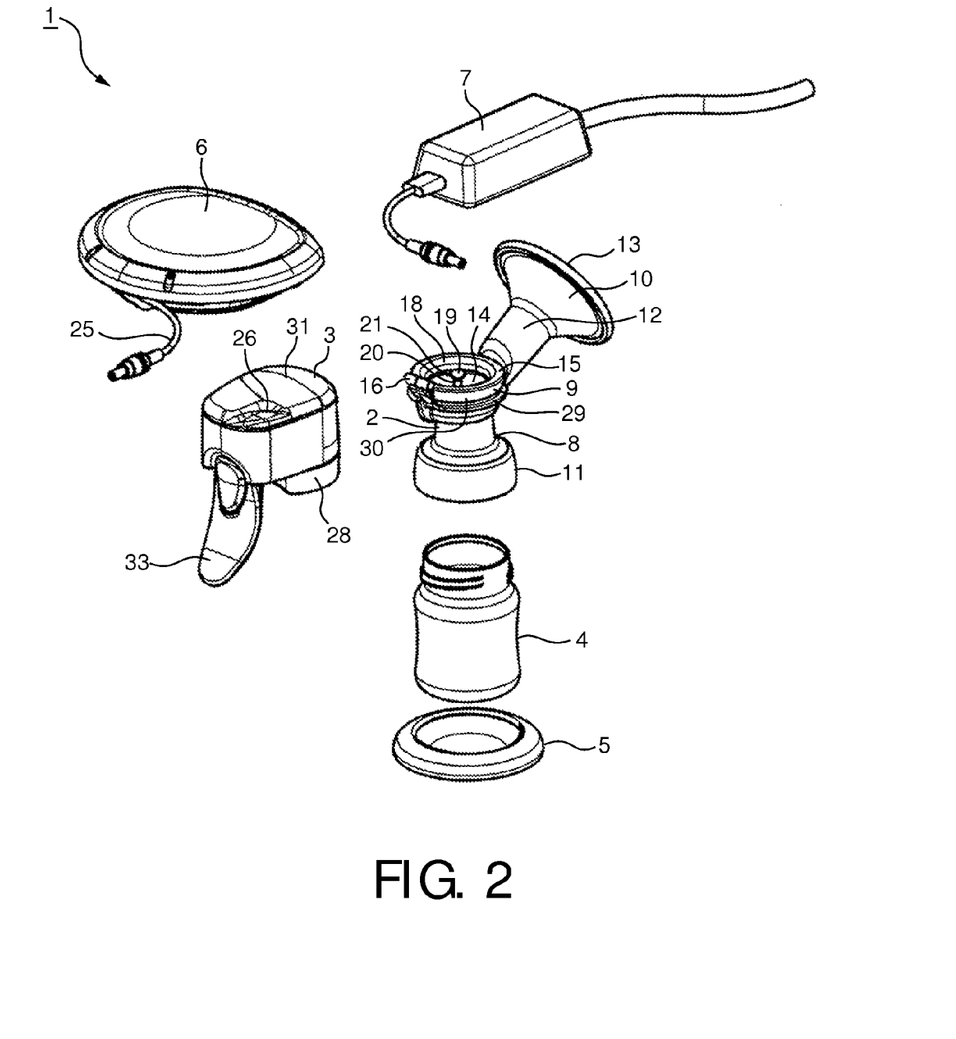
FIG. 2 is an exploded perspective view of the breast pump system shown in FIG. 1 with a motorised head for a breast pump according to one aspect of the present invention.

Referring to FIG. 2, the breast pump system 1 further includes a battery pack 6 and a mains power supply unit (PSU) 7. The body 2 comprises a neck 8, a cup 9 supported on the neck 8 and a trumpet 10 projecting from the side of the cup 9. The flared portion 11 extends from the bottom of the neck 8 and is provided with an internal thread (not shown) for screwing the feeding bottle 4 onto the body 2.

The trumpet 10 is inclined upwards and, in use, receives the nipple and surrounding breast portion of the user and is sealed thereby. A passageway 12 extends from an open, distal end 13 of the trumpet 10 through the bottom of the cup 9 and the neck 8 to the open, bottom end of the neck 8. A valve (not shown) operable by a piston means 14, is provided between the cup 9 and the neck 8. The valve (not shown) is closed when the pressure in the cup 9 drops relative to the pressure in the neck 8 and opens when the pressure in the cup 9 rises to exceed the pressure in the neck 8.

The piston means 14 comprises a diaphragm 15 received within the cup 9 which is cup shaped and formed from elastomeric material. A rim 16 of the diaphragm 15 is turned back on itself to form a channel 17 (refer to FIG. 6) which receives an upper end 18 of the cup 9 to secure the diaphragm 15 in the cup 9. An actuating element 19 extends from the centre of the diaphragm 15 towards the upper end 18 of the cup 9. The actuating element 19 comprises a stem 20 and a bulbous end 21, distal to the diaphragm 15, which is attachable to a drive mechanism 22 of the motorised head 3, as will be explained in detail hereinafter.

The battery pack 6 has a plug 25 which is received in a socket 26 in the motorised head 3 to supply power of the motorised head 3. Alternatively, the power supply unit 7 can be plugged directly into the socket 26 of the motorised head 3 to power the motorised head. The PSU 7 may also be used to supply power to the battery pack 6. The battery pack 6 and the PSU 7 are conventional, and so no further discussion of these components will be given herein.

Figure 3:
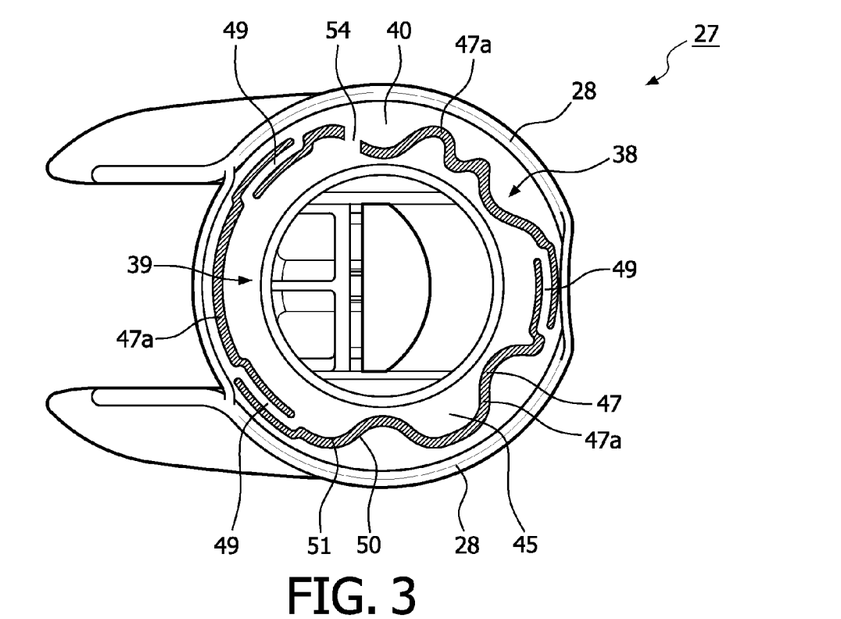
FIG. 3 is a bottom plan view of a head element of the motorised head shown in FIG. 2.
Figure 4:
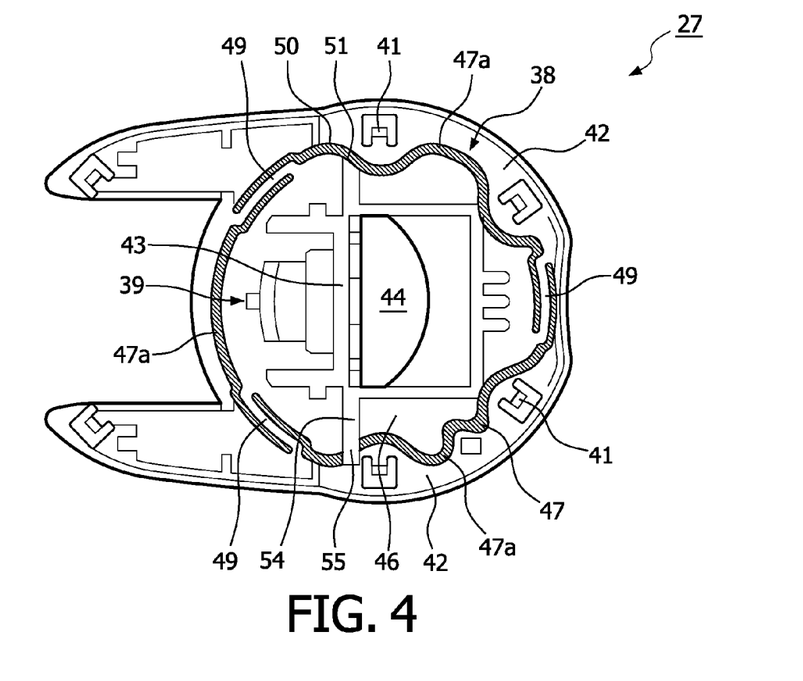
FIG. 4 is a top plan view of the head element shown in FIG. 3.

Referring to FIGS. 3 and 4, the motorised head 3 comprises a base element 27, which is large enough to extend over the upper end of the cup 9. A pair of arcuate flanges 28 extend from the base element 27, and each flange 28 clips over a radially extending ridge 29 on an outer surface 30 of the cup 9.

The motorised head 3 further comprises a housing 31, and an arm 32 extends from the back of the housing 31 through a cutaway in the housing 31. The arm 32 acts as an operating lever for operating the motorised head 3, and hence the breast pump, as will become apparent hereinafter. The arm 32 is pivotally mounted within the housing 31 so that pressing the arm 32 towards the cup 9 closes a switch (not shown). The arm 32 is outwardly biased by a spring (not shown) within the housing 31. The housing 31 is mounted to the base element 27 of the motorised head 3 by known means.

The motorised head 3 houses a motor unit (refer to FIG. 5) including a motor 35, a drive mechanism 36 which is driven by the motor 35, and a printed circuit board (not shown) which carries the unit's control circuit.

The base element 27 includes a body mounting portion 38 and a motor mounting portion 39. The body mounting portion 38 extends around the motor mounting portion 39, and the pair of arcuate flanges 28 extend from a lower face 40 of the body mounting portion 38 around an outer edge thereof. Hook portions 41 extend from an opposing upper face 42 of the body mounting portion 38. The housing 31 is connectable to the hook portions 41 of the body mounting portion 38 to form an outer enclosure of the motorised head 3.

A support 43 for the motor 35 and the drive mechanism 36 is formed on the motor mounting portion 39, and an aperture 44 is formed through the motor mounting portion 39 between a lower face 45 and an upper face 46 thereof.

The upper face 42 of the body mounting portion 38 and the upper face 46 of the motor mounting portion 39 lie on the same plane and the lower face 43 of the body mounting portion and the lower face 45 of the motor mounting portion 39 lie on the same plane. The motor mounting portion 39 is spaced from the body mounting portion 38 by a through-channel 47 which extends substantially there between said mounting portions 38, 39.

Figure 5:
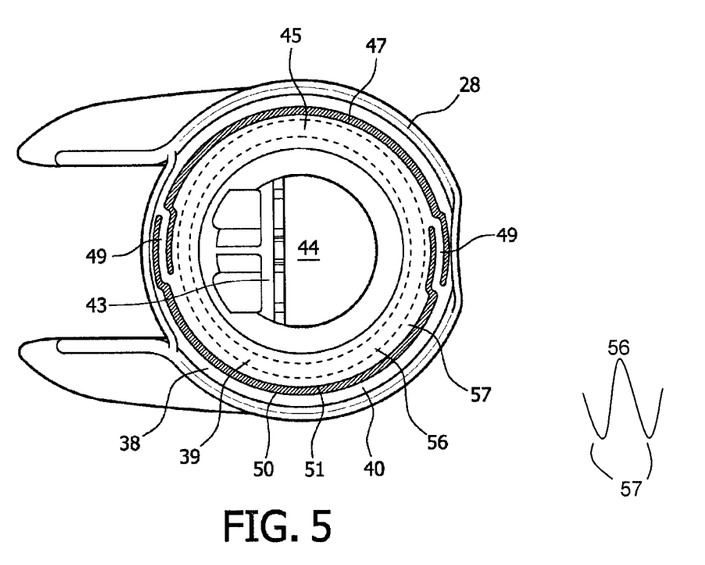
FIG. 5 is a bottom plan view of a head element according to another embodiment of the motorised head shown in FIG. 2.

Linking members or "decoupling bridges" 49 extend between the body mounting portion 38 and the motor mounting portion 39 across the through-channel 47. Although three linking members are shown in FIGS. 3 and 4, it will be appreciated that the number of linking members 49 is not limited thereto and that any number of linking members 49 may be used, for example, two linking members are shown in FIG. 5. A minimal number of linking members 49 are utilised to minimise the mechanical coupling between the body mounting portion 38 and the motor mounting portion 39 so that vibrations transmitted to the body mounting portion 38, and hence the body 2 and feeding bottle 4, are effectively reduced, as will become apparent hereinafter.

Each linking member 49 extends between the body mounting portion 38 at one end and the motor mounting portion 39 at a distal end thereof. The linking members 49 are resiliently deformable and are each able to flex relative to the body mounting portion 38 and the motor mounting portion 39.

The body mounting portion 38, the motor mounting portion 39 and the linking members 49 are all integrally formed to form the base element 27. Each of the body mounting portion 38, motor mounting portion 39 and the linking members 49 are seperably defined by removing material from the base element 27 to form each section 47a of the through-channel 47. Alternatively, the base element 27 of the motorised head 3 may be formed with the through-channel 47 formed therein.

Each linking member 49 extends substantially parallel in the through-channel 47 between side walls 50, 51 of the body mounting portion and the motor mounting portion 38, 39 respectively which define the through-channel 47. This allows each linking member 49 to be of suitable length to maximise the deformability of each linking member 49 to allow greater deflection between the body mounting portion 38 and the motor mounting portion 39 whilst minimising the width of the through-channel 47 between the side walls 50, 51.

Although in the above description, the linking members 49 are integrally formed with the body mounting portion 38 and motor mounting portion 39, it will be understood that in an alternative embodiment each linking member 49 may be a separate component which is fixedly mounted to each mounting portion 38, 39 and is formed from a resiliently deformable material, such as rubber.

In the embodiment show in FIG. 5, the through-channel 47 extends in a circumferential manner to form a circular motor mounting portion 39. However, the invention is not limited thereto and, as shown in FIGS. 3 and 4, the through-channel 47 may comprise a number of wavey curved portions to avoid other features of the base element 27, for example the hook portions 41 formed on the body and motor mounting portions 38, 39. The linking members 39 are evenly spaced in the through-channel 47 around the motor mounting portion 39.

The drive mechanism 22 comprises a connecting rod 53 which connects to the actuating element 19 of the piston means 40 to drive said piston means 40 in a reciprocal manner. The connecting rod 53 extends through the aperture 44 in the motor mounting portion 39 along an axis which extends through the base element 27, equidistant from each linking member 49. Therefore, when the motorised head 3 is operated, as will be explained below, no moment acts on the base element 27 and a generally uniform force is applied to each linking member 49.

A mechanical block or deflection limiting member 54 extends from the upper face 46 of the motor mounting portion 39 and extends across the through-channel 47 to be disposed above the upper face 42 of the body mounting portion 38. A remote end 55 of the deflection limiting member 54 is spaced above the body mounting portion 38 by a predetermined distance, so that during normal operation of the breast pump system 1 the deflection limiting member 54 does not contact the upper face 42 of the body mounting portion 38, but in a situation of unsymmetrical loading the distal end of the deflection limiting member 54 contacts the upper face 42 of the body mounting portion 38 to limit the maximal displacement applied to each linking member 49, as will be explained hereinafter.

Although only one deflection limiting member 54 is shown in the Figures, it will be appreciated that deflection limiting members are associated with each linking member 49 to limit the maximal displacement and thereby maximal material stress applied to the respective linking member 49. By limiting the deformation of each linking member 49, the maximum material stresses are retained within limits to increase robustness, in case of shock as well as during normal use. The deflection limiting members can absorb the impact forces and extend from the motor mounting portion 39 to above and below the upper and lower faces of the body mounting portion 38 respectively.

The lower faces 40, 45 of the body mounting portion 38 and motor mounting portion 39 respectively are formed to have a sinuous cross section with a plurality of peaks 56 and troughs 57 defined thereon. Although in this embodiment, each of the lower faces 40, 45 has a sinuous form to simplify manufacture, it will be appreciated that in an alternative embodiment only the lower face 45 of the motor mounting portion 39 may have a sinuous form and the lower face 40 of the body mounting portion 38 may be planer.

Although in this embodiment, the lower face 45 of the motor mounting portion 39 has a sinuous form with a plurality of peaks 56 and troughs 57, it will be appreciated that in an alternative embodiment the lower face 45 has any form of surface with raised portions and recessed portions (not shown), such that a contact area of the motor mounting portion lower face 45 is minimised, for example dimples.

Arrangement of the breast pump system 1 and, in particular, the motorised head 3 will now be described with reference to FIGS. 2 to 6.

The body mounting portion 38, motor mounting portion 39 and plurality of linking members 49 are integrally formed. The motor 35 and drive mechanism 22 are fixedly mounted to the support 43 for said components on the motor mounting portion 39. The motor 35 and drive mechanism 22 are fixedly mounted to the support 43 by known means. The motor 35 and drive mechanism 22 extend above the upper face 42 of the motor mounting portion 39 and the drive mechanism connecting rod 53 extends through the aperture 44 formed in the motor mounting portion 39 to a lower side thereof.

The housing 31 is attached to the base element 27 by means of the hook portions 41 formed on the body mounting portion 38, to form the outer enclosure of the motorised head 3. As discussed above, the arm 32 extends from the motorised head 3 and is pivotally attached thereto. The feeding bottle 4 is threadingly engaged with the flared portion 11 of the body 2.

To fixedly connect the motorised head 3 to the body 2, the base element 27 of the motorised head 3 is located against an upper locating surface 58 of the diaphragm 15 which extends over the upper end 18 of the cup 9. The locating surface 58, which extends over the upper end 18 of the cup 9, forms a resiliently deformable locating surface against which the base element 27 locates. In this arrangement the base element 27 extends over the upper end 18 of the cup 9 and the arcuate flanges 28 extend down over the outer surface 30 of the cup 9 to communicate with the circumferentially extending ridge 29 extending around the cup 9.

Figure 6:
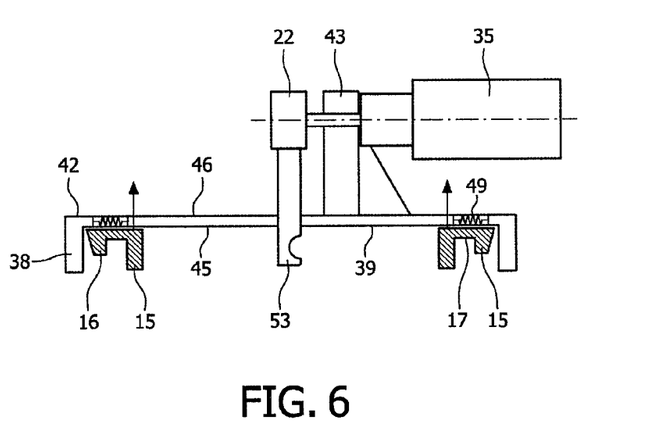
FIG. 6 is a simplified cross sectional view of the motorised head shown in FIG. 2.

In this arrangement, the lower face 40 of the body mounting portion 38 of the base element 27 locates against an outer circumferentially extending section 59 of the locating surface 58. As the user urges the motorised head 3 towards the body 2 of the breast pump system 1 the lower face 40 of the body mounting portion 38 is urged against the outer section 59 of the upper surface 58 and said surface is resiliently deformed. The arcuate flanges 28 locate over the circumferentially extending ridge 29 of the cup 9 and the outer section 58 of the upper surface 58 urges the body mounting portion 38 away from the ridge 29 such that the body mounting portion 38 is fixedly mounted to the cup 9.

As the motorised head 3 is fixedly connected to the body 2, the drive mechanism connecting rod 53 connects with the bulbous end 21 of the actuating element 19 extending from the diaphragm 15. Therefore, the connecting rod 53 is disposed to actuate the actuating element 19, and hence the piston means 14, as will be explained hereinafter.

When the base element 27 is located against the locating surface 58 of the diaphragm 15, an outer edge of the motor mounting portion 39 is disposed above an inner circumferentially extending section 60 of the locating surface 58 such that a section of the lower face 45 of the motor mounting portion locates against the locating upper surface 58. In particular, the peaks 56 of the motor mounting portion lower face 45 locate against said locating surface 58.

Operation of the breast pump system 1 will now be described in detail with reference to FIGS. 5 to 8.

To operate the breast pump system 1, a user connects a power supply in the form of the battery pack 6 or the power supply unit 7 to the motorised head 3. Said user then holds the breast pump system 1 by the body 2 and disposes a nipple and the surrounding breast in the trumpet 10 such that the trumpet 10 seals against the user's breast. To operate the breast pump system 1, the user then depresses the arm 32 and lever 33 towards the body 2 which depresses the contact switch (not shown) and activates the motor 35. The motor 35 drives the drive mechanism 22 such that the connecting rod 53 is moved in a reciprocal manner and, because said connecting rod 53 is attached to the actuating element 19 of the diaphragm, the actuating element 19 is reciprocally driven such that the diaphragm 15 strokes up and down and the piston means 14 effects pumping. The system means 14 is reciprocally driven by a predetermined stroke of the connecting rod 53 to create a cyclic vacuum in the body 2 and trumpet 10 in order to encourage the expression of milk from the user's breast. Similarly, to stop operation of the breast pump system 1, the user releases the arm 32 which disengages the switch (not shown) and the motor 35 and drive mechanism 36 stop.

When the breast pump system 1 is operated and the motor 35 drives the drive mechanism 36 to operate the piston means 14 in a reciprocal manner, via the connecting rod 53 and actuating element 19, the motor 35 and drive mechanism 36 vibrate and this vibration is transmitted to the motor mounting portion 39 to which the motor 35 and drive mechanism 36 are fixedly mounted. In a conventional system, this vibration is transmitted directly to the body 2 and feeding bottle 4 due to a direct rigid attachment of the motorised head thereto, in particular, the base element and the arcuate flanges to the body. In the embodiment of the present invention, the vibration is transmitted directly to the motor mounting portion 39 and the motor mounting portion 39 is therefore urged to vibrate when the breast pump system is operable. However, the motor mounting portion 39 is capable of moving substantially independently of the body mounting portion 38 because it is decoupled therefrom by the through-channel 47 which spaces the motor mounting portion 39 from the body mounting portion 38. However, the motor mounting portion 39 is held in position by each of the linking members 29 which extend between the body mounting portion 38 and the motor mounting portion 39. Each linking member 49 is deformable, such that it flexes when the motor mounting portion 39 vibrates to minimise the transfer of vibration to the body mounting portion 38. The motor mounting portion 39 also locates against the inner circumferentially extending portion 60 of the locating upper surface 58. The peaks 56 of the sinuous lower face 45 of the motor mounting portion 39 support the motor mounting portion 39 on the locating upper surface 58.

Figure 7:
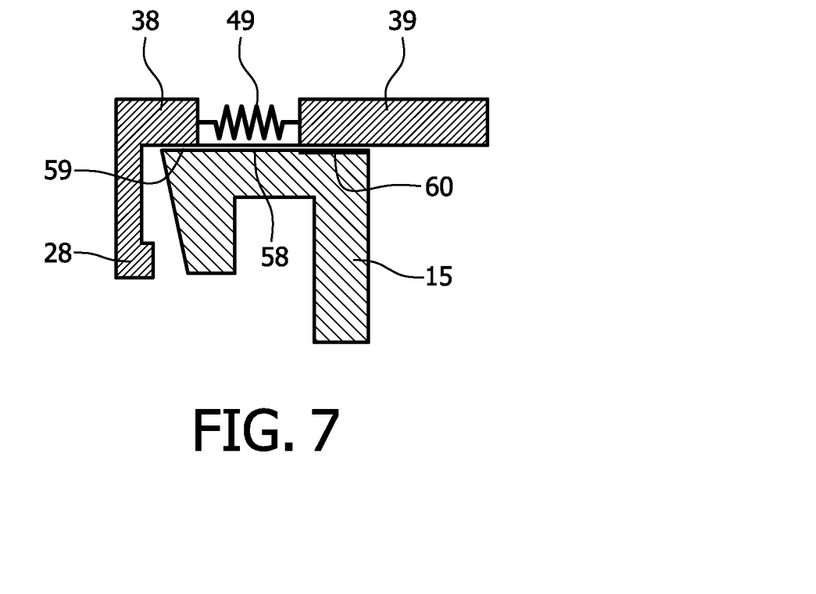
FIG. 7 is a simplified cross sectional side view of the motorised head shown in FIG. 6.

When the drive mechanism 22 is operable and pulls up the diaphragm 15, which is formed from silicone rubber, via the connecting rod 53 and the drive mechanism 22 to create a vacuum, the lower face 45 of the motor mounting portion 39 is pulled towards the locating surface 58. The sinuous form of the lower face 45 means that only the peaks 56 of said lower face 45 contact the locating surface 58 and so the contact area of the lower face 45 on the locating surface 58 is reduced. Therefore, the limited number of contact points defined by the peaks 56 between the motor mounting portion 39 and the resiliently deformable locating surface 58 locally compress the resiliently deformable locating upper surface 58 and due to the local deformations in the locating surface 58, vibration energy is more effectively dissipated and the vibration dampened which results in a lower noise level.

The sinuous lower face 45 of the motor mounting portion 39 therefore takes advantage of the acoustic dampening properties of the silicone rubber diaphragm upon which said face 45 rests.

Furthermore, the transmission of vibration energy between the motor mounting portion 39 and the body mounting portion 38 is reduced because the body mounting portion 38 is decoupled from the motor mounting portion 39 apart from the linking members 40 which extend there between. Each of these linking members 49 connects these two components to each other, however, each linking member 49 is flexible so that it can deform and the motor mounting portion 39 can move relative to the body mounting portion 38.

In this embodiment, a lower side of each linking member 49 rests on the locating surface 58. Each linking member 49 has a sufficient length in order to allow deformations during use, while keeping the maximum material stresses below critical levels.

The flexible coupling formed by the linking members 49 greatly reduces the vibrations are transmitted to the body mounting portion 38 from the motor mounting portion 39. Therefore, vibrations do not easily transmit from the motor 35 to the body 2 and the feeding bottle 4 and so the effective sound level emitted by the body 2 and feeding bottle 4 is reduced. In view of the above, the noise level of the breast pump system 1 is greatly reduced by reduction of the so called "structure born" sound.

As discussed above, the housing 31 is fixedly connected to the base element 27, and the base element 27 extends over the cup 9, wherein the body mounting portion 38, and also the motor mounting portion 39, locates against the locating surface 58 of the diaphragm 15 which extends over the top of the cup 9. Therefore, the air gaps of the outer enclosure surrounding the pump mechanism, in particular the motor and drive mechanism, are diminished or closed-off which reduces the noise emitted directly from the motor and drive mechanism to the outside.

In a situation when the motorised head 3 is removed from the body 2 of the breast pump, for example when a user removes the head for cleaning or the breast pump is dropped, then the motor mounting portion 38 is pulled away from the body mounting portion 38 until the connecting rod 53 disconnects from the actuating element 19. This exerts an increased force on the linking members 49, which must be supported by said members 49. However, to limit the displacement of the motor mounting portion 38, the deflection limiting member 54 extends from the motor mounting portion 39 to above the body mounting portion 38, such that when the motor mounting portion 38 is displaced by a predetermined distance, the remote end 55 of the deflection limiting member 54 contact the upper face 42 of the body mounting portion 38 and further displacement is prevented. Furthermore, the deflection limiting members 54 allow the manual placement or removal by the user of the motorised pump head from the pump body, without exceeding the maximum material stress limit which would otherwise cause damage thereto.

Figure 8:
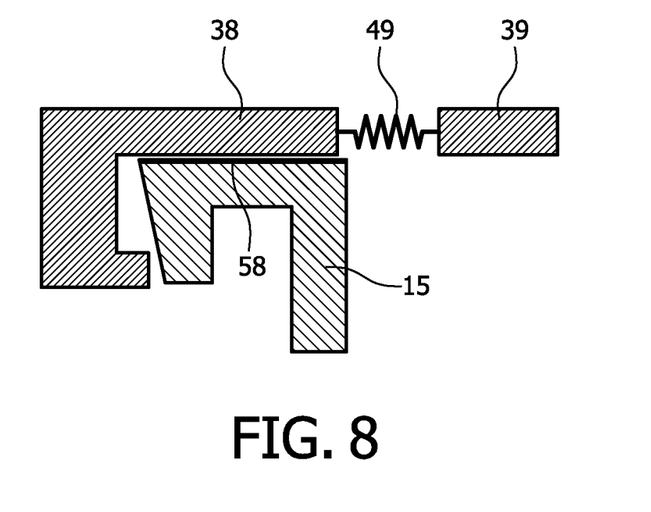
FIG. 8 is a cross sectional side view of another embodiment of the motorised head shown in FIG. 6.

Referring now to FIG. 8, another embodiment of the base element of the motorised head is shown. This embodiment of the base element is generally the same as the base element 27 discussed above and so a detailed description will be omitted and components and features in common will be designated the same numbering.

In this embodiment, the body mounting portion 38 locates against the locating surface 58 of the diaphragm 15 when the motorised head 3 is mounted to the body 2. However, the motor mounting portion 39 is disposed above the cup 9 such that it is spaced from the upper end 18 of the cup by the through-channel 47 and so does not contact the locating surface 49. Therefore, in this embodiment the motor mounting portion 39 is supported by the linking members 49 only, and is decoupled from the remaining components of the breast pump.

Although in the above embodiments the diaphragm is described extending over the top of the cup to form the locating surface 58, it will be understood that in an alternative embodiment the diaphragm may not extend over the upper end of the cup to form the locating surface 58, and the locating surface may be formed from a separate component extending from the upper end of the cup which is resiliently deformable.

Although in the above embodiments the invention is described in respect to a drive mechanism with a reciprocal movement it will be understood that the invention is not limited thereto, and the invention would be effective for use with a continuously rotating motor and further motor and drive-train combinations, for example a crankshaft, a linear motor, a wormwheel and a rack and pinion system.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claims in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A motorized head for a breast pump configured to reduce a transfer of vibrations caused by a motor or drive mechanism to a body of the breast pump, the head comprising:
   a motor unit portion supporting a motor and a drive mechanism for driving the pump;
   a body mounting portion fixedly mountable to a body of the breast pump;
   a through-channel extending substantially between and separating the motor and body mounting portions;
   a plurality of resiliently deformable linking members, each member is configured to
      extend substantially parallel in the through-channel between the body and motor mounting portions connecting the body mounting portion and the motor mounting portion, and
      comprise a length maximizing its deformability to allow deflection between the body and motor mounting portions and minimizing a width of the through-channel, such that the transfer of vibration caused by the motor or drive mechanism to the breast pump body is reduced.

2. The motorized head according to claim 1, wherein the body mounting portion extends around a periphery of the motor mounting portion.

3. The motorized head according to claim 2, wherein a section of each resiliently deformable linking member extends parallel to lower and upper edges of the motor mounting portion.

4. The motorized head according to claim 2, wherein a section of each resiliently deformable linking member extends parallel to an edge of the motor mounting portion.

5. The motorized head according to claim 3, wherein through-channel is defined between the motor mounting portion and the body mounting portion, and each resiliently deformable linking member extends therebetween.

6. The motorized head according to claim 3, wherein the plurality of resiliently deformable linking members comprises two resiliently deformable members positioned diametrically opposite each other.

7. The motorized head according to claim 3, wherein the body mounting portion, the motor mounting portion and the plurality of resiliently deformable linking members are integrally formed.

8. The motorized head according to claim 3, wherein the body mounting portion is fixedly locatable against a locating surface of a diaphragm on the body of the breast pump.

9. The motorized head according to claim 8, wherein the motor mounting portion includes a lower face locatable against the locating surface, and the locating surface is resiliently deformable.

10. The motorized head according to claim 9, wherein the lower face includes raised portions locatable against the locating surface to minimize a contact area of said lower face against said locating surface.

11. The motorized head according to claim 9, wherein said lower face has a sinuous form and raised peaks.

12. The motorized head according to claim 9, further comprising at least one flange that extends from the body mounting portion and is configured to fixedly mount to the body of the breast pump.

13. A hand held powered breast pump configured to reduce a transfer of vibrations caused by a motor or drive mechanism, the breast pump comprising:
   a body having a breast receiving portion for attaching a vessel;
   a motor mounting portion supporting a motor and a drive mechanism for driving the pump;
   a body mounting portion fixedly mountable to a body of the breast pump;
   a through-channel extending substantially between and separating the motor and body mounting portions;
   a plurality of resiliently deformable linking members, each member configured to
      extend substantially parallel in the through-channel between the body and motor mounting portions connecting the body mounting portion and the motor mounting portion, and
      comprise a length maximizing its deformability to allow deflection between the body and motor mounting portions and minimizing a width of the through-channel, such that the transfer of vibration caused by the motor or drive mechanism to the breast pump body is reduced; and
   a piston configured to attach to the drive mechanism for effecting pumping.

14. The hand held powered breast pump according to claim 13, wherein the piston comprises a resilient diaphragm having a locating surface defined by an engaging part of the resilient diaphragm.

15. The hand held powered breast pump according to claim 14, wherein said locating surface includes raised portions and the face of the motor mounting portion is configured to locate against said raised portions.

* * * * *